(12) United States Patent
Witham

(10) Patent No.: US 8,653,443 B2
(45) Date of Patent: Feb. 18, 2014

(54) NEUTRAL PARTICLE MICROSCOPE

(76) Inventor: Philip James Witham, Portland, OR (US)

( * ) Notice: Subject to any disclaimer, the term of this patent is extended or adjusted under 35 U.S.C. 154(b) by 0 days.

(21) Appl. No.: 13/535,236

(22) Filed: Jun. 27, 2012

(65) Prior Publication Data
US 2013/0001413 A1 Jan. 3, 2013

Related U.S. Application Data

(60) Provisional application No. 61/571,521, filed on Jun. 29, 2011.

(51) Int. Cl.
*H05H 3/02* (2006.01)
*H05H 3/04* (2006.01)

(52) U.S. Cl.
USPC .......................................................... 250/251

(58) Field of Classification Search
USPC ................................................ 250/251, 396 R
See application file for complete search history.

(56) References Cited

U.S. PATENT DOCUMENTS

| | | | | |
|---|---|---|---|---|
| 4,751,393 | A * | 6/1988 | Corey et al. | 250/492.2 |
| 5,512,746 | A * | 4/1996 | Saito | 850/41 |
| 6,489,622 | B1 * | 12/2002 | Chen et al. | 250/492.21 |
| 6,590,210 | B1 * | 7/2003 | Essers | 850/9 |
| 6,977,376 | B2 * | 12/2005 | Fukuda et al. | 850/1 |
| 7,554,097 | B2 | 6/2009 | Ward et al. | |
| 7,601,953 | B2 | 10/2009 | Ward et al. | |
| 7,683,318 | B2 * | 3/2010 | Bunton et al. | 250/309 |
| 2003/0075691 | A1 * | 4/2003 | Abe | 250/491.1 |
| 2003/0168595 | A1 * | 9/2003 | Danilatos | 250/310 |
| 2004/0079884 | A1 * | 4/2004 | Khursheed et al. | 250/311 |
| 2007/0158580 | A1 | 7/2007 | Ward et al. | |
| 2008/0185509 | A1 * | 8/2008 | Knowles | 250/251 |

OTHER PUBLICATIONS

Focusing of molecular beams for the development of new tools for nanoscience and nanotechnology—Sabrina Eder* , Thomas Reisinger, Bodil Holst Dep. of Physics and Technology University of Bergen Bergen, Norway Gianangelo Bracco Department of Physics, University of Genoa, Italy, and Dep. of Physics and Technology, University of Bergen Bergen, Norway.*
Atom "Pinhole Camera" with Nanometer Resolution V. I. Balykina, P. A. Borisova, V. S. Letokhova, P. N. Melent'eva, S. N. Rudneva, A. P. Cherkuna, A. P. Akimenkob, P. Yu. Apel'b, and V. A. Skuratovb a Institute of Spectroscopy, Russian Academy of Sciences, Troitsk, Moscow region, 142190.*

(Continued)

*Primary Examiner* — Jack Berman
*Assistant Examiner* — Sean Luck
(74) *Attorney, Agent, or Firm* — Robert J. Ireland

(57) ABSTRACT

The invention includes a source stream of neutral particles (neutral atoms and neutral molecules, but not neutrons) in free molecular flow, a beam forming element disposed within the source stream having at least one small aperture located proximal to the sample allowing part of the source stream to pass through the aperture as a beam of neutral particles directed at the sample for revealing the sample, a control positioner for scanning the beam of neutral particles over or through portions of said sample surface, optionally one or more detector nozzles having an inlet positioned to collect neutral particles proceeding from or through the sample surface in free molecular flow, at least one detector, the detector arranged to sense neutral particles proceeding from the sample, and a processor connected to the detector and control positioner for generating an image of said sample.

20 Claims, 14 Drawing Sheets

(56) References Cited

OTHER PUBLICATIONS

M. Koch, S. Rehbein, G. Schmahl, T. Reisinger, G. Bracco, W. E. Ernst, and B. Holst, Journal of Microscopy, Imaging with neutral atoms—a new matter—wave microscope, 2008, 229:1.

D.A. MacLaren, B. Holst, D.J. Riley, W. Allison, Surface Review and Letters, 2003, 10:249.

University of Cambridge, Cavendish Lab, Surface Physics website http://www-sp.phy.cam.ac.uk/research/mirror.php3.

F. Shimizu, Phys. Rev. Lett., 2002, 88, 12 123201.

R.B. Doak, R.E. Grisenti, S. Rehbein, G. Schmahl, J.P. Toennies, and C. Woll, Phys. Rev. Lett., 1999, 83, 4229.

V.I. Balykin, V.S. Leokhov, T.B. Ovchinnikov, and A.I. Sidorov, Phys. Rev. Lett., 1988, 60, 2137.

C.V. Saba, P.A. Barton, M.G. Boshier, I.G. Hughs, P. Rosenbusch, B.E. Sauer, and E.A. Hinds, Phys. Rev. Lett., 1999, 82, 468.

D.C. Lau, A.I. Sidorov, G.I. Opat, R.J. McLean, W.J. Rowlands and P. Hannaford, European Physical Journal, 1999, D 5, 193.

B. Holst, W. Aliison, Nature, 1997, 390, 244.

K. Fladischer, H. Reingruber, T. Reisinger, V. Mayrhofer, W.E. Ernst, A.E. Ross, D.A. MacLaren, W. Allison, D. Litwin, J. Galas, S. Sitarek, P. Nieto, D. Barredo, D. Farias, R. Miranda, B. Surma, A. Miros, B. Piatkowski, E. Sondergard and B. Holst, New Journal of Physics, 2010, 12, 033018.

Barredo, G. Laurent, F. Calleja, P. Nieto, J.J. Hinarehos, A.L. Vazquez De Parga, D. Farias, and R. Miranda, Applied Physics Letters, 2010, 96, 081901.

D. Barredo, F. Calleja, P. Nieto, J.J. Hinarejos, G. Laurent, A.L. Vazquez De Parga, D. Farias, R. Miranda, Advanced materials 2008, 20, Issue 18, 3492.

J. G. King, W.R. Bigas, Nature, 1969, 222, 261.

J.C. Weaver, J.G. King, Proc.Nat.Acad.Sci, 1973, 70, No. 10, 2781.

J. Braun, P.K. Day, J.P. Toennies, G. Witte, and E. Neher, Rev. Sci. Instrum., 1997, 68, Issue 8, 3001.

D.R. Miller, G. Scoles Editor, Atomic and Molecular Beam Methods, (Oxford University Press, New York), 1988, pp. 14-51.

H. Pauly, Atom, Molecule, and Cluster Beams I, (Springer, Berlin 2000).

M.P. Grams, A.M. Cook, J.H. Turner and R.B. Doak, J. Phys. D: Appl. Phys., 2006, 39, 930.

T. Reisinger, G. Bracco, S. Rehbein, G. Schmahl, W. E. Ernst and B. Holst, J. Phys Chem A, 2007, 111, No. 49, 12620.

R. G. Livesey, Foundations of Vacuum Science and Technology, J. M. Lafferty editor, (Wiley Interscience, New Your, 1998), 81-137.

D. J. Riley, M. Mann, D. A. MacLaren, P. C. Dastoor, and W. Allison, Nano Letters 2003, 3, 10, 1455.

M. Dekieviet, D. Dubbers, M. Klein, U. Pieles, and C. Schmidt, Rev. Sci. Instrum, 2000, 71, 2015.

R.B. Doak, J. Phys.: Condens. Matter 2004, 16, No. 29, S2863.

S. Maruyama, H. Kinbara, H. Hayashi, D. Kimura, Nano. and Micro. Thermophys. Eng., 1997, 1 Issue 1, 39.

H.C. Schewe, B.S. Zhaol, G. Meijer and W. Schollkopf, New J. of Phys., 2009, 11, 113030.

S. Eder, T. Reisinger, B. Holst, G. Bracco, 9th IEEE Conference on Nanotechnology, (IEEE, 2009), 391.

P. Witham and E. Sanchez, A Simple Approach to Neutral Atom Microscopy, Review of Scientific Instruments, Oct. 2011, 82, 103705.

P. J. Witham, E.J. Sanchez, Journal of Microscopy, Increased resolution in neutral atom microscopy, Aug. 17, 2012, p. 1-5, 10.1111, Royal Microscopical Society.

B. Holst, G. Bracco, Springer, Surface Science Techniques, p. 354-357.

H. Seiler, Journal of Applied Physics, Secondary electron emission in the scanning electron microscope, p. 1-19.

* cited by examiner

ID
NEUTRAL PARTICLE MICROSCOPE

CROSS-REFERENCE TO RELATED APPLICATION

This application claims priority under 35 U.S.C. §119(e)(1) to U.S. Ser. No. 61/571,521, filed Jun. 29, 2011, which is hereby incorporated by reference in its entirety.

TECHNICAL FIELD OF THE INVENTION

This disclosure generally relates to Neutral Atom Microscopy (NAM) and, more particularly, to apparatus and methods that provide relatively high resolution imaging using non-charged atom or molecule (herein "neutral particle") beams. This field has also been termed Atomic deBroglie Microscopy and also Scanning Helium Microscopy (SHeM).

BACKGROUND

Microscopes provide imaging in two general modes, transmission mode and reflection mode. Transmission mode relates to illumination through a sample, where reflection mode relates to illumination that returns from the surface of the sample. Various historic microscope apparatus and method enabling both modes of microscopy rely on different types of physical interactions to provide magnified imaging of a sample.

For example, conventional optical microscopes rely upon light reflecting from, or transmitting through a sample. The light is then passed through focusing lenses or mirrors to achieve high magnification. The resolution limit of conventional optical microscopes is related to the light wavelength of hundreds of nanometers. Electron and ion microscopes rely on charged particles, focused using lenses that employ electric or magnetic fields, and offer significantly higher resolution potential due to the shorter deBroglie wavelength of the relatively high-Momentum particles used, in most cases under 0.1 nm. The deBroglie wavelength of a particle can be thought of as a scale of distance over which a particle interacts, similarly to the wavelength of light. This wavelength is, $\lambda = h/m_0 V$, where h is Planck's constant, $m_0$ is the particle mass and V the particle velocity.

The Scanning Electron Microscope and Helium Ion Microscope rely upon a charged particle beam generally of 1,000 to 50,000 eV energy directed at the sample, as compared to 2 to 3 eV for visible light. Albeit the imaging resolution is extremely good, but the high kinetic energy and the charge of the particles directed at the sample can be destructive to and/or reactive with the sample. In addition, the resulting electrical charging of insulating samples can interfere with successful imaging. At such energies, the beam particles also penetrate many atomic layers through the sample and therefore do not exclusively image the surface atomic layer of the sample, but may instead produce images from some greater depth range through the sample, as is the case for conventional optical microscopes for wavelength reasons.

For over two decades scientists have pursued imaging surfaces using a focused beam of neutrally charged atoms or molecules. Imaging without high energy beams while achieving high resolution is theoretically possible this way, because the high mass of atoms compared to electrons produces a short deBroglie wavelength, under 0.1 nm even at less than 0.1 eV energy. Molecular beam experiments show that certain neutral atoms and molecules at this energy scatter from the top atomic layer of samples, and imaging with this method could result in new information about materials and objects that cannot be readily obtained using previous forms of microscopy.

However, previous attempts at a neutral particle microscope have produced poor image signal to noise ratio and/or poor resolution due to a combination of problems. One problem is the difficulty of finding a suitable focusing element able to produce a high intensity, sharply focused beam spot of neutral particles. Neutral atoms and molecules are not strongly affected by electric or magnetic fields, and for the most part, scatter randomly off of mirror surfaces, making it difficult to focus, control, and direct the beam for imaging purposes. A second problem is the poor sensitivity of available neutral atom or neutral molecule detectors, which can only detect a very small fraction of the particles entering them. Probably the first images published from a neutral atom microscope were published in 2008, and were obtained in transmission mode.[1] They were of poor signal to noise ratio and had somewhat better than 2 μm resolution. Prior to the disclosed invention, no published images improved significantly on these and none were obtained in reflection mode.

[1] Imaging with neutral atoms—a new matter-wave microscope, M. Koch, S. Rehbein, G. Schmahl, T. Reisinger, G. Bracco, W. E. Ernst, and B. Hoist., Journal of Microscopy 229: 1 (2008).

Accordingly a need exists for a microscope apparatus and method which provides reflective mode and transmission mode non-destructive imaging using neutral particles.

SUMMARY OF INVENTION

This disclosure generally relates to neutral particle microscope methods and systems, including such systems and methods that utilize a "pinhole" aperture to form a neutral particle beam without a focusing element, and detector nozzle technology that increases neutral particle detector performance. The terms neutral atom and neutral molecule are used synonymously herein as neutral particles, as the inventive apparatus may use either or combinations of the same, specifically excepting neutrons. The term "neutral particle" will be used herein to reference both neutral atoms and neutral molecules with the stated exclusion of neutrons.

In accordance with one embodiment of the invention, a stream of neutrally charged particles such as Helium atoms, are first emitted by a source nozzle and then formed into a beam by a very small aperture proximally located to the sample. "Proximal" means the aperture is not more than 100 μm away from the sample in order to maintain the relative small spot size of the beam required for high resolution imaging. The aperture's mechanism for beam formation is the blocking of all particles of the neutral particle stream, except those traveling in the desired direction that pass through the aperture as a narrowed beam of neutral particles.

The neutral particle beam reaches the sample and some of the reflected or transmitted particles are detected by a gas particle detector. A scanner controllably changes the relative position of the sample and aperture allowing for a mapping of particle detections over the sample surface, thereby providing information that is converted into sample images by a processor. The sample is easier to maneuver for scanning purposes, but changing position of the aperture or the source nozzle can be performed to accomplish the same objective of altering the relative position of the sample to the beam.

Detection by the gas particle detector is enhanced through the use of a detector nozzle having an input end located close to the sample, positioned to receive a favorable cross-section of neutral particles coming from the sample after impact or transmission. In accordance with one embodiment, the detector nozzle has an inlet that is placeable close to the sample, requiring the inlet end to be relatively small and shaped to accommodate the aperture holder. The detector nozzle outlet may be much larger, matching the volume enclosing the detector for connection. Detected pressure is enhanced by the relatively small inlet area being located close to the sample where the reflected or transmitted pressure (neutral particle density) is higher. The enclosing volume of the detector nozzle and surrounding the detector prevents escape of the neutral particles that enter the detector nozzle, except for that portion of neutral particles that escape backwards out the inlet.

Further aspects of the invention will be described herein in the following portions of the specification wherein the detailed description is for fully disclosing preferred embodiments without placing limitations thereon.

BRIEF DESORPTION OF THE DRAWING FIGURES

BRIEF DESCRIPTION OF THE INVENTION

Figure 1:
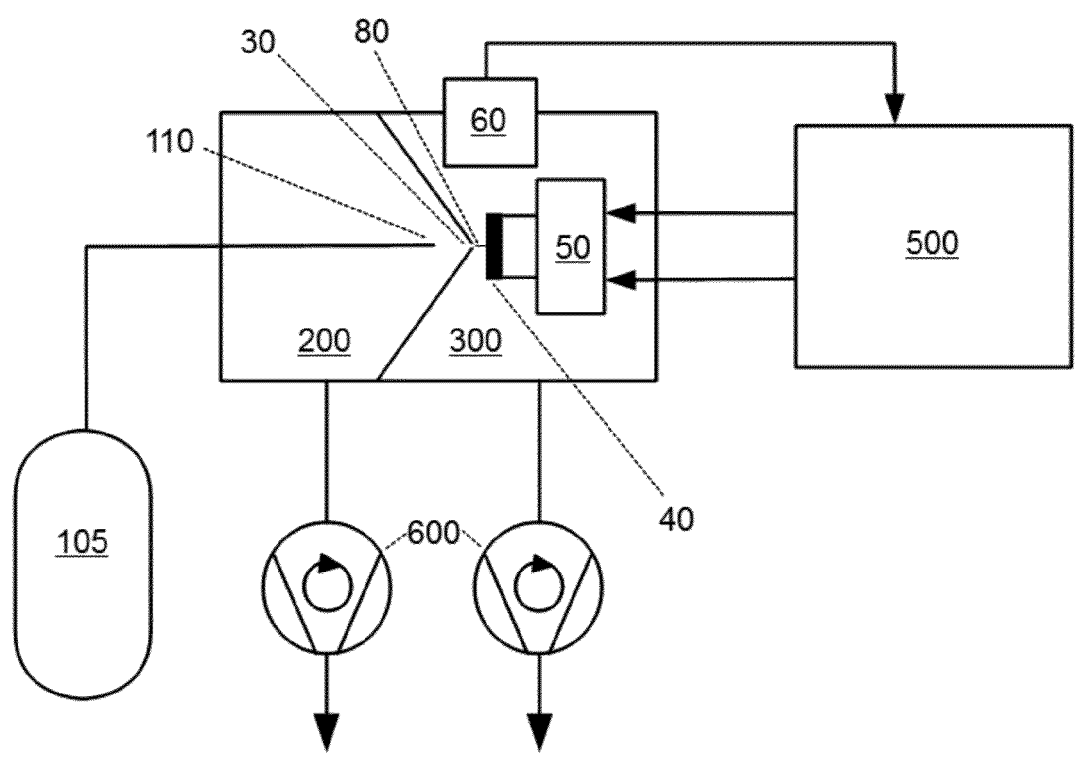
FIG. 1 is a diagram illustrating the overall system diagrammatically by block diagram.

The following description is provided to enable any person having ordinary skill in the art to make the disclosed neutral particle microscope, and is provided in the context of microscopy. Various modifications to the embodiments will be readily apparent to those skilled in the art, and the principles and configurations defined herein may be applied to other embodiments and applications without departing from the spirit and scope of the invention. Thus, applicant's invention is not intended to be limited to the preferred and other embodiments described herein, but is to be accorded the widest scope consistent with the principles, features and teachings disclosed herein.

As shown in FIGS. 1-3 and 6, a gas supply 105 emits a directional stream of neutral particles through a source nozzle 110, which could be neutral atoms or neutral molecules, specifically excluding neutrons. The particle type used in the preferred embodiment was Helium, but other potentially useful particles include Duterium ($D_2$), Neon, Argon, $H_2O$, Krypton, and Xenon. The "source" vacuum chamber 200 is maintained at pressures that allow free molecular flow of the neutral particles. Some of the gas stream travels in the direction of the sample 40, and passes through the small aperture 30 ("pinhole") continuing towards the sample 40 as a defined neutral particle beam 80. Once through the aperture 30, the neutral particle beam 80 passes in free molecular flow through pressures provided and maintained in the sample vacuum chamber 300.

Figure 6:
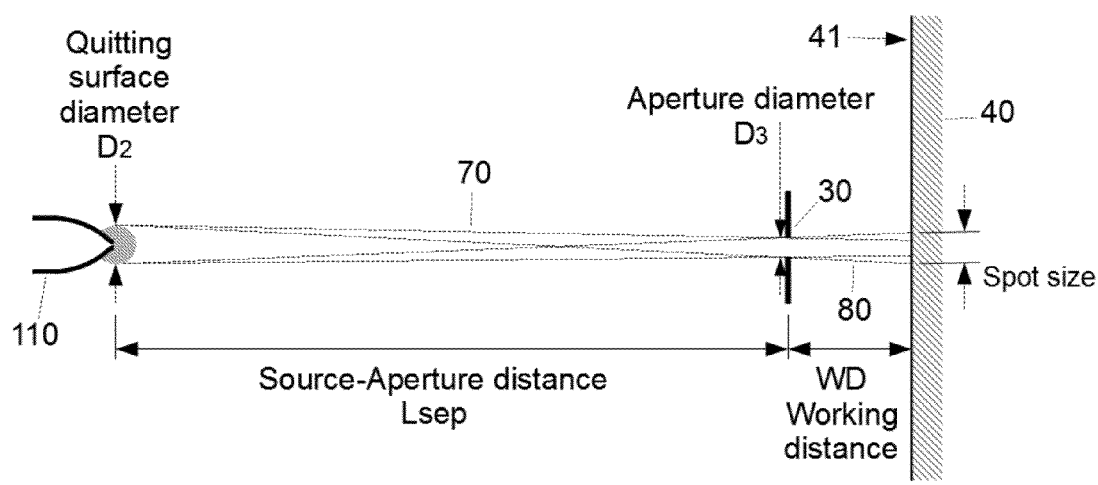
FIG. 6 is a depiction of the beam geometry.

As the beam 80 passes into the sample chamber 300, it will diverge in spot size the further it travels from the aperture 30. As a small spot size is desired, the sample 40 is positioned in close proximity to the aperture 30 such that the neutral particle beam 80 reaches the sample while the beam's spot size is still relatively small. The adequately small spot size impacting the sample is achieved through a combination of an aperture of less than 1 μm in diameter and a working distance between the sample surface and the aperture of less than 100 μm as depicted in FIG. 6. In other words, the aperture 30 must be proximal to the sample. "Proximal" means the aperture is not more than 100 μm away from the sample 40 in order to maintain the relative small spot size of the neutral particle beam 80 required for high resolution imaging.

Figure 2:
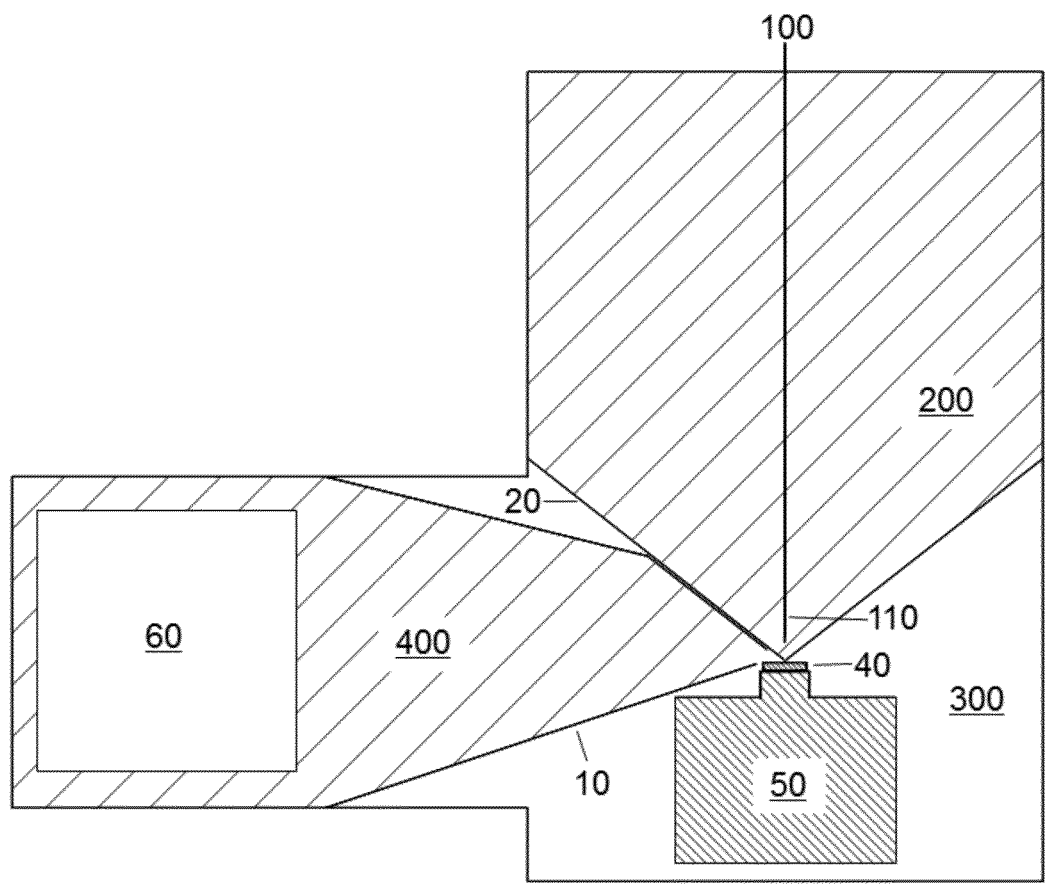
FIG. 2 is a diagram of a side view cross section illustrating the configuration for reflection mode.

In the preferred embodiment in reflection mode as shown configured in FIG. 2, at least one detector 60 senses beam particles reflected off of the sample 40 over some range of angles. Each detector 60 produces a signal representing the rate, pressure or density of neutral particles reflecting or scattering off of the surface of the sample 40. More detectors 60 positioned at different radial perspectives around the sample 40 improve performance and versatility.

Figure 3:
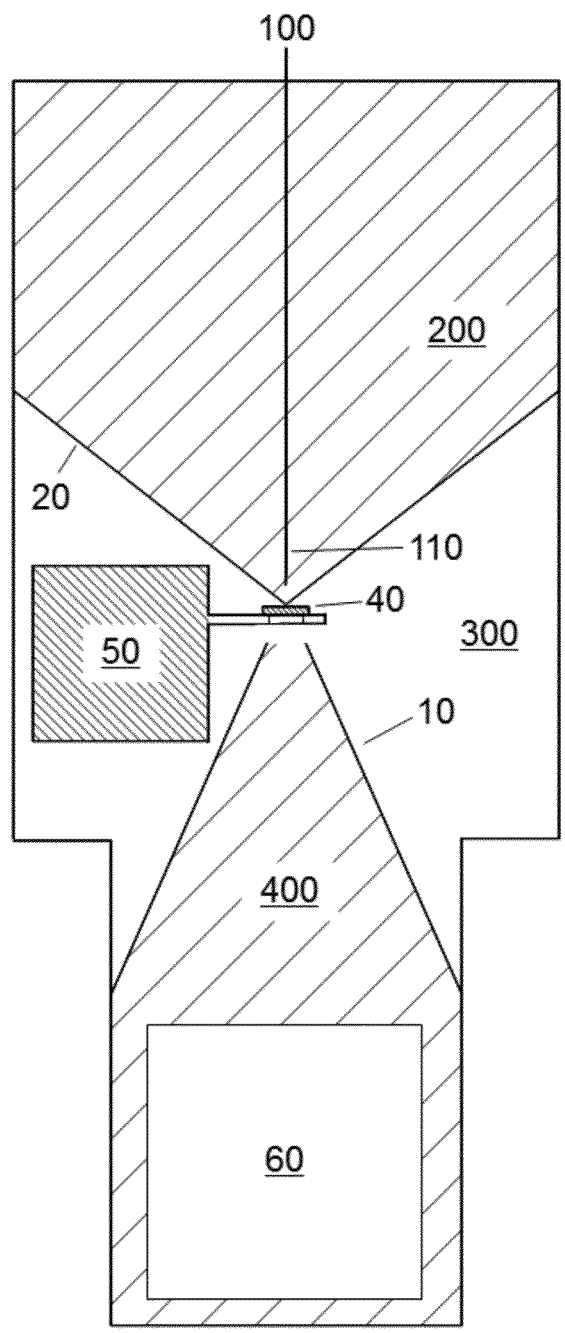
FIG. 3 is a diagram of side view cross section illustrating the configuration for transmission mode.

In other embodiments in transmission mode as shown configured in FIG. 3, at least one detector 60 is located to sense beam 80 particles that have passed through the sample 40.

The sample 40 and aperture 30 are mechanically scanned relative to each other, meaning either the sample 40 or the aperture 30 may be moved, or both as shown in FIGS. 1-4. A computer or data processor 500 depicted in FIG. 1 collects the detector's 60 measurements, mapping them into a two dimensional array in synchrony with the mechanical scanning performed by the scanner or positioner 50. The data is then converted to an image by scaling the measurement data range to image black and white limits or color map limits, whichever is desired.

Figure 7:
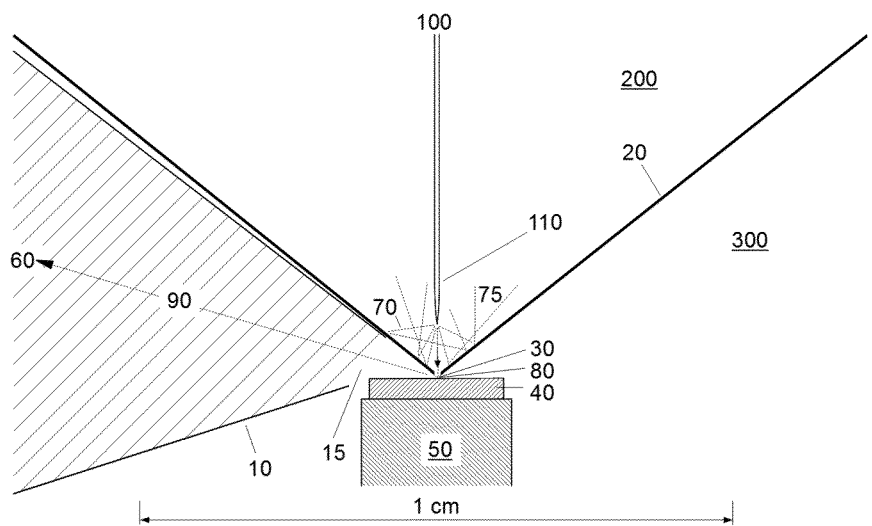
FIG. 7 is a side view cross section diagram illustrating the configuration for reflection mode at a closer scale than FIG. 2.
Figure 8:
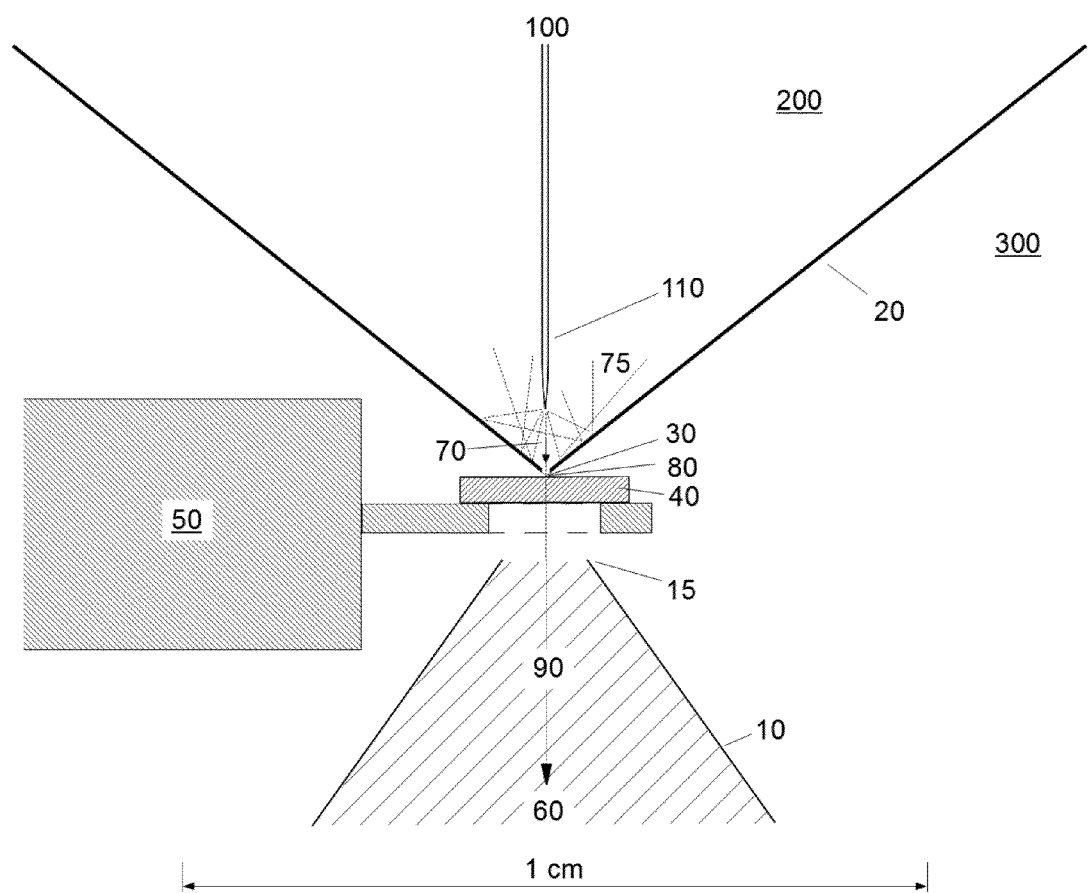
FIG. 8 is a side view cross section diagram illustrating the configuration for transmission mode at a closer scale than FIG. 3.

As illustrated in FIGS. 7-8, source gas particles 75 not passing through the aperture 30 but rather impacting the "interior" of the aperture holder 20 or source chamber 200 are removed by a vacuum pumping system 600. Gas within the sample chamber 300 not detected by the detector 60 is also removed by a vacuum pumping system 600.

On the source side, vacuum 200 is needed to ensure free molecular flow conditions between the source 110 and aperture 30. On the sample side 300 of the aperture, the gas pressure must be low enough to ensure free molecular flow between the aperture 30 and sample 40, and between the sample 40 and the detector inlet 15.

In addition, the background partial pressure of the chosen beam gas in the sample chamber 300 must be sufficiently low that the background level of this gas in the detector(s) 60 does not interfere with image quality. If it were too high, it would produce an excessive noise level in the images. For this reason the source system must be separated from the sample chamber 300. These evacuated chambers communicate through the beam-forming aperture hole 30.

Figure 4:
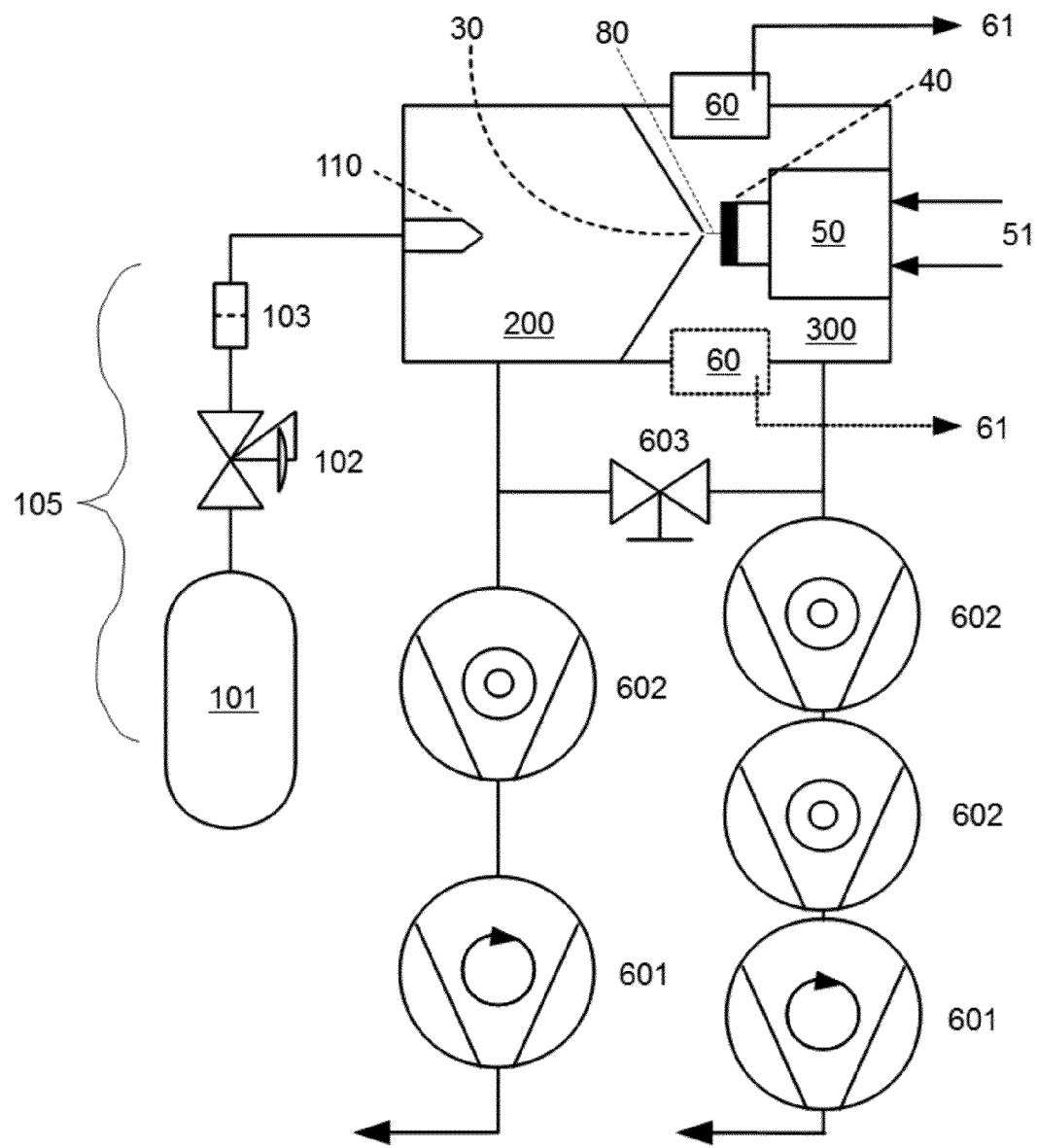
FIG. 4 is a schematic illustrating a suitable vacuum system.

As illustrated in FIG. 4, these vacuum criteria can be met in one embodiment with the block diagram arrangement of vacuum chambers, pumps and valves. Two foreline vacuum pumps 601 provide the rough pumping needed to back the three high vacuum pumps 602. In the preferred embodiment, these are common two-stage rotary vane foreline pumps and turbomolecular high vacuum pumps. Two turbomolecular pumps are used in series on the sample chamber side 300 in order to attain a sufficiently high compression ratio for Helium, This is also the reason for using two separate foreline pumps, as the compression ratio must be high enough to keep the sample chamber helium background pressure low, for best image signal to noise ratio. Some high vacuum pump types have higher helium compression ratio performance and fewer pumps would be needed. Other pump types, such as diffusion pumps, and more or fewer pumps could be used.

Valve 603 is opened when venting to atmosphere or rough pumping the system from atmospheric pressure to prevent a large pressure difference from occurring across the aperture 30. Not shown are various valves and components that are not necessary to the function of the microscope but which are common place in vacuum apparatus, such as a vent valve and foreline isolation valves to allow shutoff without venting.

Source

Figure 5A:
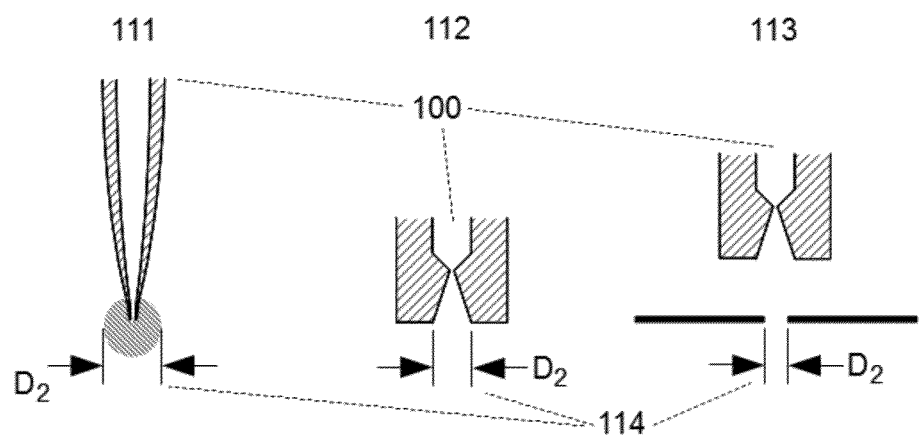
FIG. 5A is a depiction of some possible source nozzle types for use with the invention.
Figure 5B:
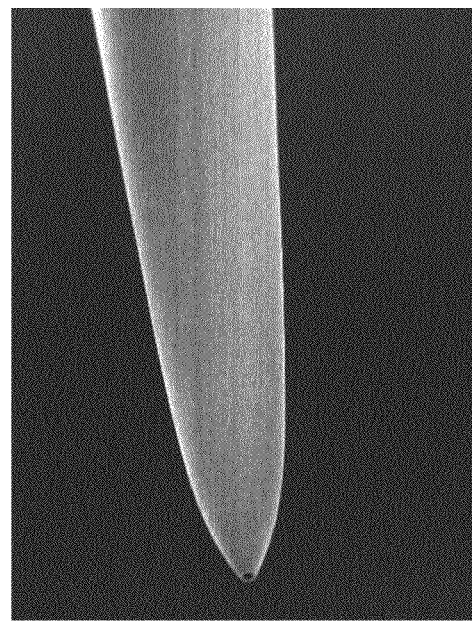
FIG. 5B is a micrograph of a free jet nozzle.

As used in the preferred embodiment and depicted in FIG. 5A, the source 110 may be a simple free jet nozzle 111 as used in molecular beam experimental apparatus and further shown by SEM Micrograph in FIG. 5B. The design of the source 110 is not claimed here or specified other than as an example, since these are common in molecular beam apparatus and many different variations will suffice as a source. It may also be of any design, for example a deLaval (converging-diverging) style nozzle 112, or a nozzle followed by an additional "skimmer" aperture 113, or a focusing element concentrating gas at the interior side of the aperture. The only requirement is that it produces a stream of gas in free molecular flow against the interior side of (beam-forming) aperture 30. In most designs, the gas source is a pressurized gas bottle 101 followed by a pressure regulator 102.

The source 110 may incorporate provisions to aid in alignment of the source 110 and aperture 30 relative positions, such as fingers or other areas that contact the interior of the aperture holder 20.

Geometry Optimization

FIG. 6 illustrates the geometry used to estimate the beam spot size on the sample 40 surface, using the following formula:

$$D_{Spot} = D_2 \frac{WD}{L_{Sep}} + D_3 \frac{WD + L_{Sep}}{L_{Sep}}$$

$D_2$ is the "quitting surface" diameter if a free jet nozzle 111 is used as the source. "Quitting surface" refers to the area surrounding a free jet nozzle 111 within which gas to gas scattering is still common due to the gas density, before the gas has expanded into free molecular flow at a lower density. This approximate sphere is the area from which all downstream source gas particles appear to originate. $D_2$ may also be the inside diameter of the final aperture of the source system if it is not a simple free jet nozzle 111.

From this calculation it can be seen that a short Working Distance (WD) produces a smaller beam spot size.

A certain minimum beam intensity (flow rate) is needed to take images of good signal to noise ratio in a reasonable period of time. Beam flow rate ($n_{beam}$, in particles/sec) can be estimated with the following formula.

$$n_{beam} = I_0 \frac{\pi}{4} \left( \frac{D_3}{L_{sep}} \right)^2 sr$$

$I_0$ is the source intensity (in particles/s×sr). From this it can be seen that increasing the aperture 30 diameter or moving the source closer will increase beam intensity. This is a compromise with resolution, since to improve resolution, the aperture diameter ($D_3$) must be reduced, and/or the source distance Lsep must be increased.

Shortening WD also allows the source 110 to aperture 30 distance Lsep and the aperture diameter $D_3$ to be reduced, with an increase in resolution resulting. For best performance, WD is reduced as far as practical without risk of contacting the sample 40. In the preferred embodiment, the aperture diameter $D_3$ is under 1 μm and WD is under 100 μm. To achieve this short working distance, the Z position of the sample 40 (position along the beam axis) can be manually adjusted for close proximity to the aperture 30. The position of the sample 40 can be monitored optically by microscope or camera observing the gap between the aperture 30 and sample 40. To achieve a closer WD, Z approach may be monitored by another means, such as capacitance, or electrical conduction, or conduction of vibration between the aperture holder 20 and sample 40, and Z approach may thus be controlled electronically.

Beam Forming Element (Aperture Holder)

Figure 14A:
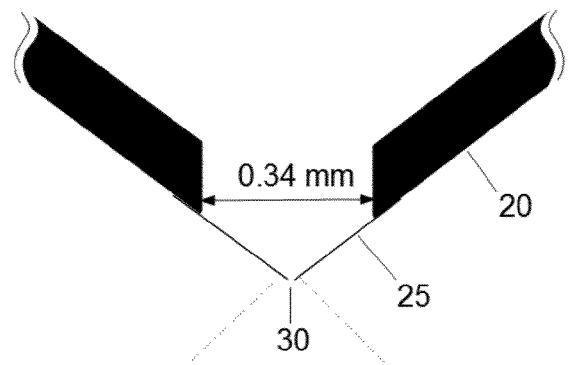
FIGS. 14A, 14B and 14C are a magnified view of the aperture hole area of the beam forming aperture in side cross section cutaway view. 14A is the preferred embodiment, magnified further in 14B, and 14C is an alternative embodiment.
Figure 14B:
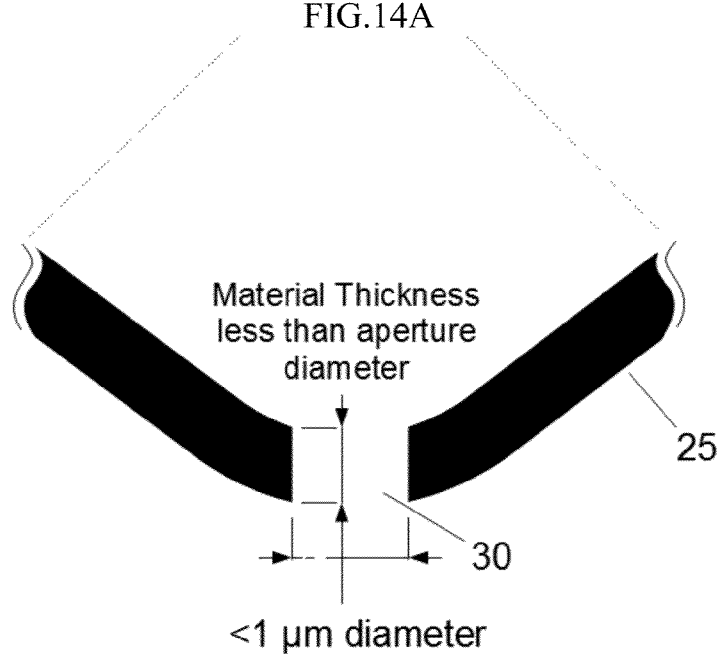

As illustrated in FIG. 7 for reflection mode and 8 for transmission mode, the close proximity of the sample 40 poses a challenge for the Beam Forming Element design, which is one of the reasons driving the conical shape in the preferred embodiment. To maintain clearance from the sample 40 and (in reflection mode) an open path to the detector 60 from the beam landing spot, the aperture holder 20 ends in an approximate cone or wedge shape. This cone points downstream, a reversal of conventional "skimmer" apertures. In the preferred embodiment, this cone or wedge shape continues to a sub-micron point where the aperture 30 is drilled, as illustrated in FIGS. 14A and 14B. This gives the greatest clearance from the sample 40 while bringing the aperture 30 as close as possible, in other words minimum WD and thus the highest resolution potential and also the greatest clearance to the detector 60 in reflection mode.

This shape also must not have too narrow a point angle or it would concentrate reflected source gas on the interior side to an excessive degree, which could scatter the beam. In the preferred embodiment, the angle measured at the aperture point across the exterior face is nominally 120 degrees, and could range from 90 degrees to just under 180 degrees. There is no requirement that this shape is a body of rotation or that it have symmetry, hence many shapes would function.

In the preferred embodiment, the material at the end of the aperture holder 20 has a thickness of less than the aperture-hole diameter, as illustrated in FIG. 14B. This prevents scattering of the beam by a buildup of gas pressure within the aperture hole, and makes the axial alignment of the source and aperture less critical. However, the main body of the aperture holder 20 must be of stronger construction such as formed aluminum.

Figure 14C:
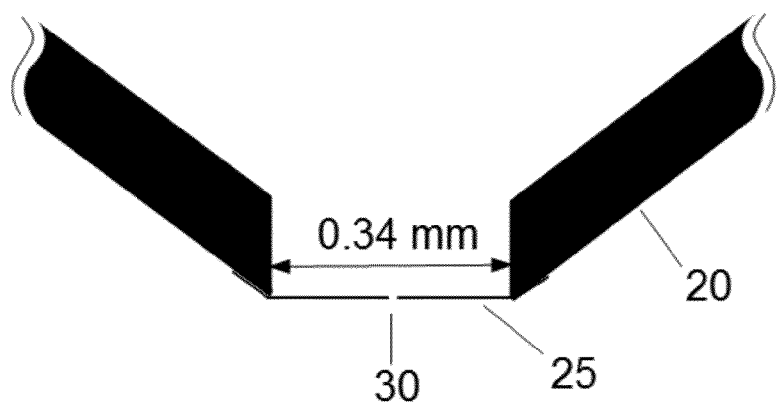

In one embodiment, the aperture holder 20 is made of three pieces. The main body is machined from metal with a large hole on the end of its cone shape. A separate cone stamped from metal sheet, about 1 cm diameter, has a small hole drilled in its tip, for instance with a number 80 drill bit. On this cone is glued (using epoxy) a flake of graphite paper pealed ("exfoliated") from Highly Oriented Pyrolytic Graphite, forming a thin membrane. Ideally the graphite flake is stamped into a cone shape before gluing but may be glued on flat, as in FIG. 14A or 14C. The small aluminum and graphite cone is then placed in a Focused Ion Beam (FIB) machine and drilled to the desired aperture diameter.

Figure 9:
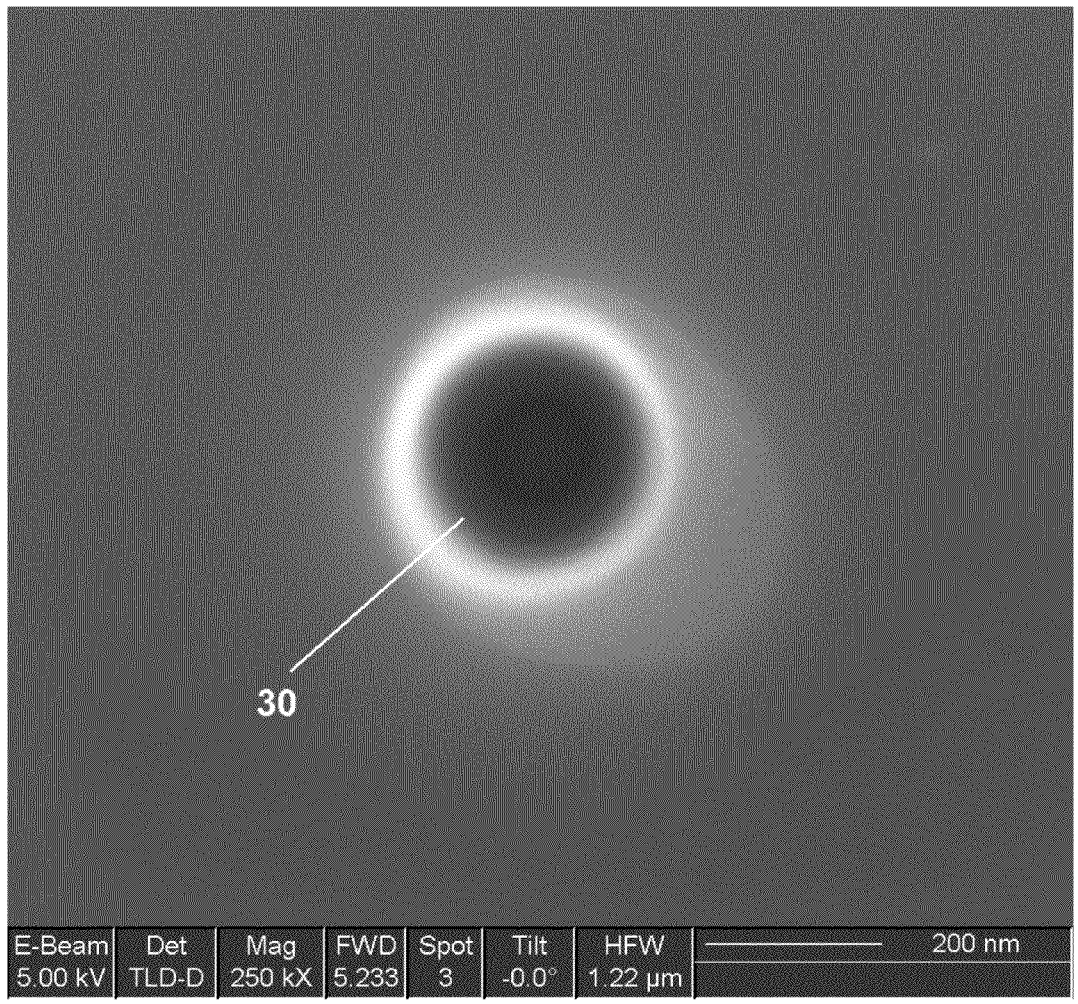
FIG. 9 is a micrograph demonstrating the aperture as drilled in graphite for the preferred embodiment.

The result of a FIB drilling the aperture is shown in FIG. 9. After drilling the metal cone and aperture are then glued (using epoxy) to the larger aperture holder body shown in earlier FIGS.

In other embodiments, materials other than graphite may form the thin membrane at the end of the aperture holder 20, such as a polymer film formed by dipping a mechanically drilled hole in a polymer solution and allowing it to dry. This would then be FIB drilled to produce the aperture 30. Part or all of the aperture holder 20 and aperture may 30 be formed by micromachining techniques in silicon or other materials.

In one embodiment, the aperture holder is replaceable by removing it from the source chamber side after disassembling the source vacuum chamber 200. This is accomplished by mounting the aperture holder 20 in a machined, cylindrical port at the junction of the source 200 and sample 300 chambers depicted in FIGS. 1 and 4. An o-ring grove is machined in the ID of this port, and an o-ring seals to an outer, cylindrical portion of the aperture holder 20 that extends from the cone shape. In other embodiments, replacing the aperture holder 20 is done through a load-lock constructed to the side or along the source axis.

The aperture holder 20 may incorporate provisions to aid in alignment of the source 110 to the aperture 30, such as by providing an area in its interior for the source 110 to contact for alignment. This could include going so far as to integrate the source 110 and aperture holder 20 together, such as by providing a ferrule and threaded clamp for holding a source nozzle tube 110 in place.

No focus or astigmatism adjustments are required, which is a speed advantage over potential focused NAM designs since making adjustments would require a number of additional scans.

Detector(s)

As depicted in FIGS. 1, 2, 3, 6, 7 and 8, a detector 60 senses some of the beam particles that have reflected from the sample 40 (reflection mode), or passed through the sample 40 (transmission mode). In the preferred embodiment, a mass-filtered detector is used. These typically operate by ionizing some of the gas particles entering the detector 60, and separating the desired (beam) gas particle 90 mass using a quadropole analyzer or a magnetic sector, then detecting the ions with a Faraday cage or electron multiplier. An example is the commercial Residual Gas Analyzer (RGA) used in one embodiment. The detector 60 output signal represents the detection rate of gas particles, or in other words the number detected within a given sample period. This rate is directly proportional to the density or pressure of the gas particles in the detector. If the particles were mass-filtered, this is a "partial pressure" signal.

A more effective but more expensive embodiment would have more than one detector 60, collecting from different angles relative to the sample 40. Two can be used for differential mode to improve signal to noise ratio. Two or more could be used to produce a pseudo-color image, or simply to provide post-scan choice of sample "illumination" direction.

He and $D_2$ are good source gas choices due to the low typical background partial pressure at mass 4, but any gas could be used simply by changing the gas supplied to the source, and selecting the corresponding mass for filtering by the detector (RGA or other mass spectrometer). Scanning a sample 40 with two or more different gasses may provide contrast information that is useful in identifying the nature of the surface material. In one embodiment, multiple gasses could be mixed for the source gas and detected nearly simultaneously by the spectrometer in one scan, for this purpose.

In reflection mode as shown in FIG. 7, the image contrast is produced at least by the sample topography. This is because the fraction of beam particles that reflect from the surface to the detector 60 changes with the angle of the surface. Thus the sample topography changes the detected gas pressure. Other contrast mechanisms are possible, as this type of microscopy is a new science.

In transmission mode as shown in FIG. 8, the image contrast is produced by the sample blocking passage of beam particles 80 to the detector 60.

Figure 10:
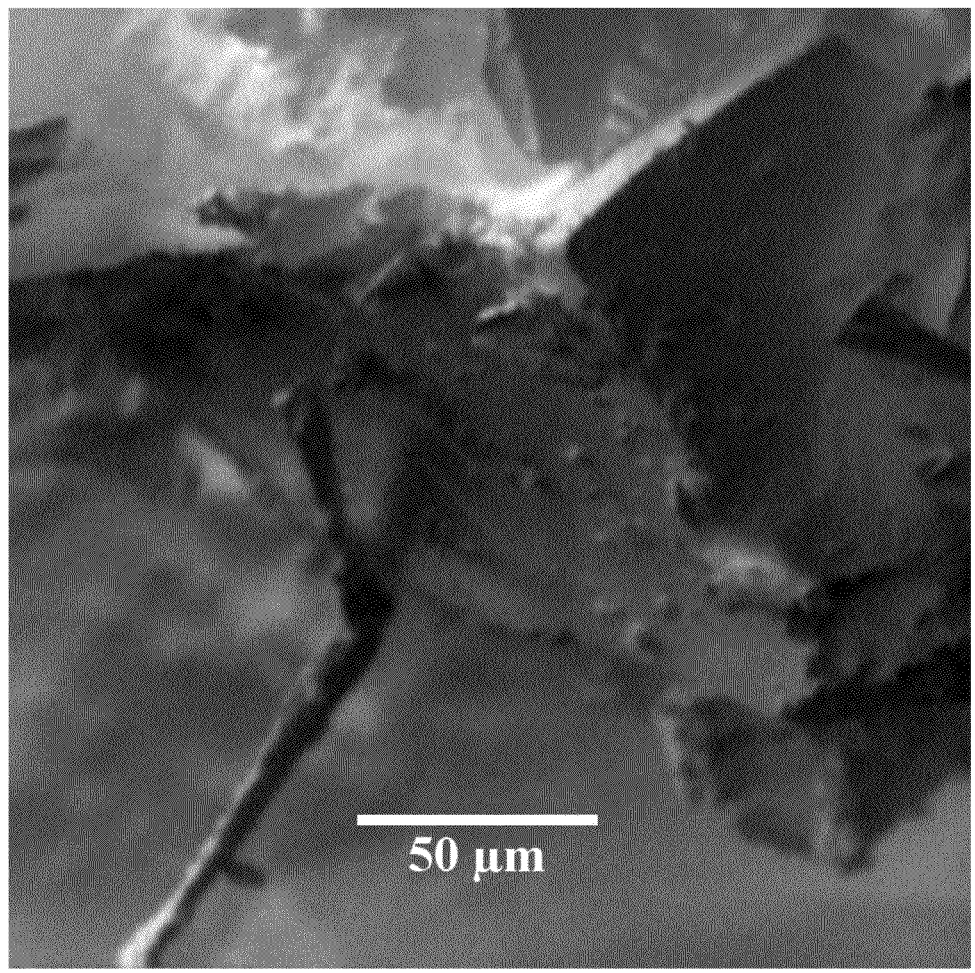
FIG. 10 is an image generated by an embodiment, the sample being NdFeB Magnet particles as imaged in reflection mode.

As shown in FIG. 10, a reflection mode image generated by the preferred embodiment of magnet particles (NdFeB), the visual effect of these contrast mechanisms is similar in many ways to optical images, but where the location of the detector 60 appears to be the source of illumination and the eye position appears to be in the direction of the beam source. This effect is similar to the appearance of SEM images taken with a secondary electron detector, where the illumination appears to come from the detector direction since surfaces angled in that direction send more electrons to the detector. Note that the image of the magnet particles would not have been possible using an electron microscope or FIB as the magnetic field would have distorted the image.

Scanner and Computer

As shown diagrammatically in FIG. 1, a personal computer or other processing system 500 is used to control the scanning of the scanner/positioner 50 and to collect the detector's 60 output signal and form an image.

In the preferred embodiment, the sample 40 is raster-scanned (controllably positioned) in two dimensions using an electro-mechanical scanner and the aperture 30 is fixed. In one embodiment the scanner is a 2-D electromagnetic actuator based on the lens focus and tracking actuator from a CD-ROM drive. This uses a moving coil assembly suspended in a permanent magnet field by four flexure wires. It is driven through two D to A converter channels and an electronic driver circuit. In another embodiment, a piezoelectric scanner with drive electronics is used or any other type of mechanical scanner that can be controlled by the computer, or which the computer can synchronize to.

In the preferred embodiment, approach of the sample 40 to the aperture 30 along the Z axis (beam axis) and large-scale positioning in X and Y are done by an electromechanical positioner 50 controlled through the computer 500. This positioner controls the base location of a separate 2D raster scanning positioner 50. The three axis of angular positioning (tilt and rotation) are similarly controlled.

Figure 13A:
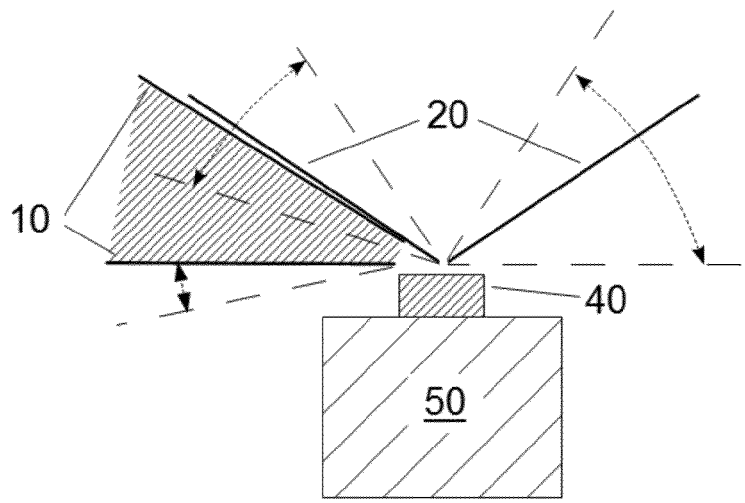
FIG. 13A is a side cross sectional view showing possible relative angles between the detector nozzle, sample, and aperture surfaces, showing how angles of aperture holder faces and detector nozzle may be changed.
Figure 13B:
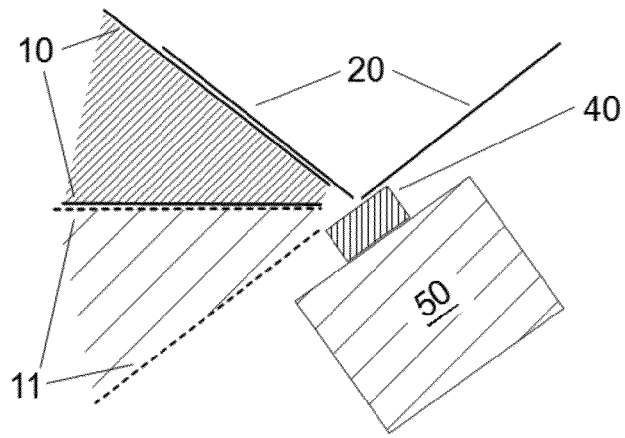
FIG. 13B is a side cross sectional view demonstrating one way additional detector nozzles can be configured, and how the sample and scanner tilt angle may be adjusted arbitrarily for optimal imaging, such as for viewing of specular reflections.

The sample 40 surface angle and XY scan plane angle may be adjusted to optimize the image illumination angle so as to increase specular reflection of the beam from the surface towards a detector, as depicted in FIG. 13B. This is accomplished by providing at least an angle adjustment in the mounting of the scanner 50 to the large-scale positioner if another control mechanism is not available.

In another embodiment, large-scale positioning is manually controlled by a screw positioner having at least control of movement on the Z axis, but more ideally three to six axis of control, as in a typical electron microscope goniometer.

In one embodiment, the sample rate is from 1 to 60 samples per second and the images are typically of between 20*20 and 800*800 pixel size.

Detector Nozzle(s)

Figure 11A:
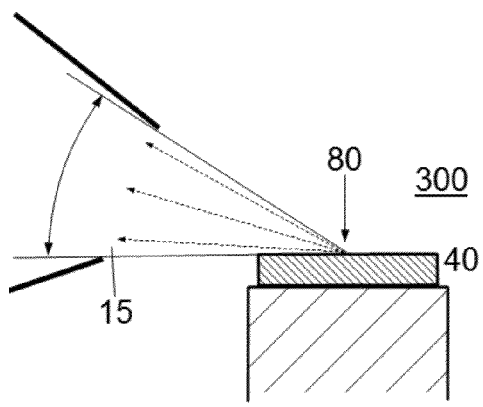
FIGS. 11A, 11B and 11C are a side view cross section diagram of the cross section view of the detector nozzle in relation with the sample, illustrating nozzle function and inlet area optimization.
Figure 11B:
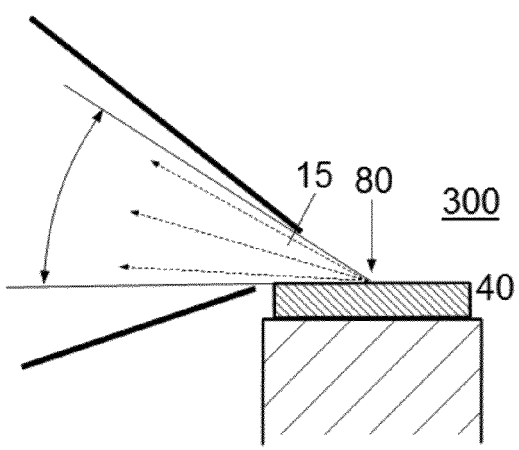
Figure 11C:
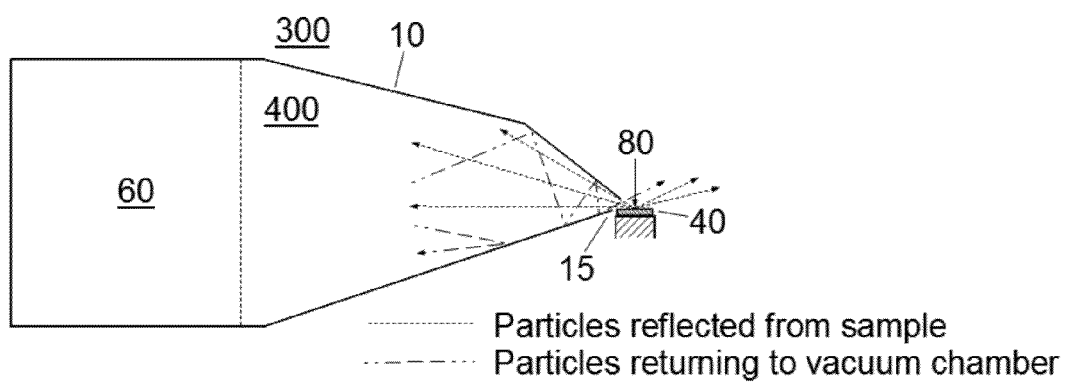
Figure 12:
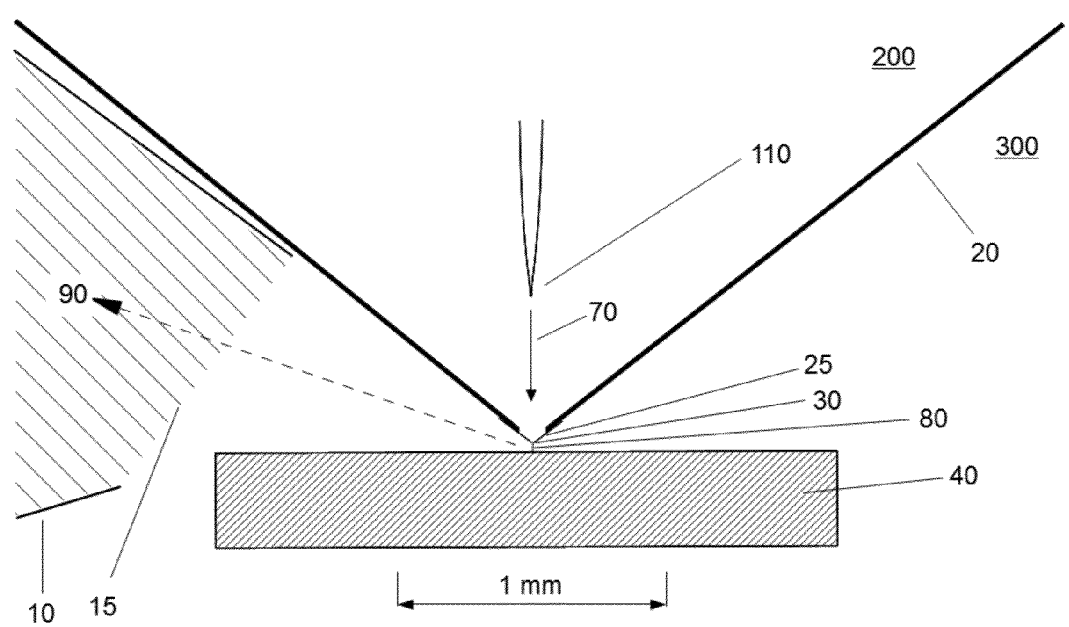
FIG. 12 is a close scale side cross section view of an embodiment in reflection mode.
Figure 13C:
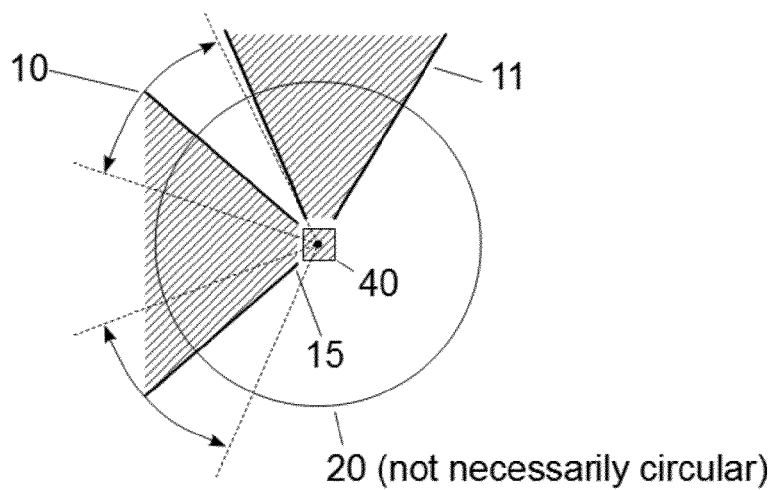
FIG. 13C is a top section view demonstrating how additional detector nozzles may be configured radially, and how the radial angle of the inlet area of the nozzle(s) may be changed.

FIGS. 11-13 depict detector nozzle 10 configurations and cross sectional views relative to the aperture 30 and sample 40 locations. Scans are very time consuming due to the poor available detector sensitivity and limited beam intensity, which is a compromise with resolution. Available detectors 60 are insensitive due to their low ionizer efficiency. Improving the detector 60 performance is critical to improving microscope resolution and/or reducing scan times.

If the partial pressure of gas sensed by the detector 60 can be increased, the Signal/Noise ratio will improve due to the improved counting statistics within a sample period. By the same factor, the sample rate can be increased to speed up scans or the beam flow rate can be reduced to improve resolution.

A detector "nozzle" 10 has been constructed as depicted in FIG. 11 which has a small inlet area 15 near the sample 40, collecting an optimal solid angle fraction of the scattered or transmitted beam particles 90. The nozzle 10 is connected on its outlet end to an enclosed volume containing the detector 60, such that the detector nozzle inlet 15 is ideally the only open area connecting the detector volume 400 to the sample vacuum chamber 300. As this nozzle inlet 15 (FIG. 11A) is made narrower (smaller in area) it can be located closer to the beam landing spot on the sample 40 (FIG. 11B). As a result, it can intercept a roughly constant included solid angle of the gas particles reflecting from (or transmitting through) the sample 40. The result is a constant in-flow of gas particles regardless of nozzle inlet 15 size (within reasonable limits), if the inlet 15 position and shape are adjusted optimally. Note that the system is operating at pressures low enough for free molecular flow.

Since this inlet area 15 is also the only area through which the gas can exit back into the sample vacuum chamber 300 from the detector volume 400, the pressure within the detector volume 400 is raised in inverse proportion to the inlet area 15. This is a free molecular flow vacuum conductance situation, where the probability of the gas particles passing out of the detector volume 400 reaches equilibrium with the incoming particles at a higher pressure as the inlet area 15 is made smaller. Another equivalent way of understanding this is that the pressure equalizes internally at roughly the same pressure produced by the gas particles incoming from the sample 40. That pressure is higher up closer to the beam landing spot since they are radiating from there and have a higher density closer in. Thus if the detector nozzle inlet 15 is made smaller, it can be moved closer to measure the pressure where it is higher.

In addition, the roughly conical shape of the nozzle 10, expanding away from the inlet 15, adds some additional boost to the internal pressure. Due to the fact that the incoming particles are radiating in straight lines from the beam landing spot on the sample 40, some of them pass straight into the nozzle inlet 15 while those passing out of the nozzle 10 must do so through random, thermal motion. Particles passing straight into the expanding area of the nozzle 10 have a decreased probability of hitting the internal walls of the nozzle 10 and thus an increased probability of traveling deep into the detector volume 400. Conversely, particles leaving, travelling outward toward the inlet area 15 face a normal chance of randomly scattering from the nozzle 10 walls and thus see the normal conductance restriction of a narrowing conical tube.

The detector has a response time constant τ due to the pressure response of the enclosed detector volume behind the opening area to the sample chamber. The response of the pressure roughly follows a first order response similar to a resistor-capacitor low pass filter. As a result of adding the nozzle 10, the pressure response time constant z will increase, proportional to v/a, where v is the enclosed detector volume 400 and a is the inlet area 15 plus any other area open to the vacuum. The result is a higher pressure and a slower tau, a compromise which can be optimized in relation to the image pixel sample time by adjusting the inlet area 15. In one embodiment, the detector volume 400 is approximately 0.23 liters, the inlet area 6 mm$^2$, and τ is roughly 0.2 seconds for helium. This is used with a detector sampling rate of four to eight per second.

For reflection mode, the inlet area 15 is also optimized in position and shape to produce the desired image illumination qualities. This is because in order to be brightly illuminated in the image, the sample area 40 should have a direct path to the detector 60 in the direction of its strongest reflection. [FIG. 12] This is similar to optical images, for instance if the detector 60 (or nozzle) inlet 15 is located close to the "horizon" of a sample surface 40, the image has the appearance of a surface lit from the side, such as the craters of the moon when they are lit close to edge-on by the sun. Similarly the position of the detector inlet 15 and sample 40 angle can be optimized for a direct illumination to enhance the potential brightness of specular surface reflections and to reduce the effect of surface topography.

In embodiments with more than one detector 60 as depicted in FIG. 13, each detector 60 ideally has its own nozzle 10 and enclosed detector volume 400, with an inlet area 15 collecting from a different included angle range.

Integrated Components

In one embodiment, the detector nozzle(s) 10 and aperture holder 20 are integrated together by bonding or machining in one piece. In another embodiment, the nozzle(s) 10 and aperture holder 20 have provisions for common alignment to the sample 40. This is useful since the most ideal detector nozzle inlet areas 15 are usually up close to the aperture holder surface 20 and close to the sample 40.

In another embodiment, the source, aperture holder 20, and detector nozzle 10 are all integrated into one assembly.

Charged Particle Microscope Uses

By substituting a charge particle source for the neutral gas source, and a charged particle detector such as an Everhart-Thornly secondary electron detector instead of the neutral particle detector and nozzle, the proximate aperture concept could be used to construct a particularly simple and small charged particle microscope. This would dispense with much of the focusing lens system and the scan coils of an SEM of FIB, and substitute the "pinhole" aperture and electromechanical scanning.

The foregoing description of the illustrated embodiments of the present invention is by way of exemplary depiction only, and other variations and modifications of the described embodiments and methods are possible in light of the foregoing teaching. Further, individual components of this invention may be implemented using one or more programmed general purpose computers, using application specific software and integrated circuits. Signal and for power connections may be hardwired, wireless, modem, etc. The embodiments described herein are not intended to be exhaustive or limiting as this invention is limited only by the following claims.

I claim:

1. A neutral particle microscope operating in reflection mode comprising:
a neutral particle source that emits through a source nozzle neutral particles towards a beam forming element, the beam forming element having an aperture holder approximately cone or wedge in shape having a sub-micron diameter aperture at the point end in flow communication with an opposing end, the opposing end constructed to receive a source stream of neutral particles; a source stream consisting of a gas released into vacuum into the opposing end, the source stream flowing downstream through the aperture holder in free molecular flow such that a beam of neutral particles exit the aperture at a location proximal to the sample surface at a beam landing spot; a control positioner for scanning the surface of the sample and the beam of neutral particles relative to each other; at least one detector arranged to sense the gas and positioned to receive neutral particles scattering from the beam landing spot in the direction of the detector in free molecular flow; and a processor connected to the detector and control positioner for generating an image of the sample surface.

2. A neutral particle microscope operating in reflection mode comprising:
a neutral particle source that emits through a source nozzle neutral particles towards a beam forming element, the beam forming element directs a beam of neutral particles in free molecular flow though a sub-micron diameter aperture to the surface of a sample at a beam landing spot; the sub-micron aperture being located at the apex of an aperture holder approximately cone or wedge in shape, a control positioner for scanning the surface of the sample and the beam of neutral particles relative to each other; a detector nozzle having an output end and an input end, the output end being connected to a detector volume, the detector volume being in flow communication with a detector that is rearranged to sense the neutral particles within the detector volume, the input end having an inlet area located and sized to receive the neutral particles scattering from the sample surface at the beam landing spot in the direction of the inlet area in free molecular flow, such that the received neutral particles are sensed at an increased pressure by the detector; and a processor connected to the detector and the control positioner for generating an image of the sample.

3. A reflection mode neutral particle microscopy method comprising:
ejecting a stream of neutral particles from a source nozzle, directing the stream of neutral particles in free molecular flow through an approximately cone or wedge shaped sub-micron diameter aperture holder exiting downstream through at least one sub-micron diameter aperture as a beam of neutral particles, the aperture proximally located to a sample surface such that the beam of neutral particles scatter from the sample surface at a beam landing spot; scanning the sample within the beam of neutral particles; locating and sizing a detector nozzle inlet area to receive neutral particles scattering from the surface of the sample at the beam landing spot in the direction of the inlet area in free molecular flow, such that the received neutral particles are sensed by a detector at an increased pressure; and processing the detector output relative to the scanning positions to generate an image of the sample surface.

4. A neutral particle microscope operating in reflection mode as claimed in claim 1, wherein the beam forming element aperture is located within 100 μm of the sample surface.

5. A neutral particle microscope operating in reflection mode as claimed in claim 1, wherein the beam forming element is constructed and arranged to accommodate the detector location relative to the beam landing spot such that neutral particles scattering from the sample surface at the beam landing spot reach the detector with a reduced probability of scattering from the beam forming element first.

6. A neutral particle microscope operating in reflection mode as claimed in claim 1, wherein the beam forming element is constructed and arranged to allow tilting of the sample surface relative to the beam of neutral particles while maintaining the proximal aperture location relative to the sample surface.

7. A neutral particle microscope operating in reflection mode as claimed in claim 1, wherein the beam forming element aperture holder continues to a sub-micron point where the aperture is drilled.

8. A neutral particle microscope operating in reflection mode as claimed in claim 1, wherein the beam forming element has more than one aperture.

9. A neutral particle microscope operating in reflection mode as claimed in claim 2, wherein the detector nozzle inlet area is sized such that the detector volume pressure response time constant is approximately equal to a sampling period.

10. A neutral particle microscope operating in reflection mode as claimed in claim 2, further including at least one additional detector nozzles,
each detector nozzle having an output end and an input end, each output end connected to a detector volume that is in flow communication with a detector that is arranged to sense the gas pressure within the detector volume,
each input end having an inlet area located and sized to receive the neutral particles scattering from the beam landing spot in the direction of the inlet area in free molecular flow, such that neutral particles received are sensed at increased pressure by the detector; and
a processor connected to the detectors and the control positioner for generating an image of the sample.

11. A neutral particle microscope operating in reflection mode as claimed in claim 2, wherein the detector nozzle inlet are is arranged to receive a roughly constant solid angle of neutral beam particles scattering from the sample surface at the beam landing spot.

12. A neutral particle microscope operating in reflection mode as claimed in claim 2, wherein the detector nozzle inlet area is sized and located such that the detector volume pressure response time constant is approximately equal to a sampling period, and thus the received neutral particles are sensed at greater pressure resulting in higher signal to noise ratio at the detector.

13. A neutral particle microscope operating in reflection mode as claimed in claim 2, wherein the detector nozzle is roughly conical in shape, expanding in area from the inlet area to the output end.

14. A neutral particle microscope operating in reflection mode as claimed in claim 2, wherein the detector nozzle inlet end area is aligned between the beam landing spot and the detector volume, such that incoming neutral particles have a straight line path from the beam landing spot to the detector volume.

15. A neutral particle microscope operating in reflection mode as claimed in 1 or 3, wherein at least one detector is enclosed with an input end, the input end having at least one aperture constructed and arranged to receive neutral particles scattering from the beam landing spot in the direction of the detector in free molecular flow.

16. A neutral particle microscope operating in reflection mode as claimed in claim 1, 2, or 3, wherein at least one detector is arranged to sense the gas density in free molecular flow.

17. A neutral particle microscope operating in reflection mode as claimed in claim 1, 2 or 4, wherein the gas is Helium.

18. A neutral particle microscope operating in reflection mode as claimed in claim 1, 2, or 3, wherein at least one detector is a Residual Gas Analyzer (RGA).

19. A neutral particle microscope operating in reflection mode as claimed in claim 1, 2, or 3, wherein the scanning involves moving the sample relative to the neutral particle beam.

20. A neutral particle microscope operating in reflection mode as claimed in claim 1, 2, or 3, wherein the scanning involves moving the neutral particle beam relative to the sample.

* * * * *